US009861129B2

United States Patent
Liu et al.

(10) Patent No.: US 9,861,129 B2
(45) Date of Patent: Jan. 9, 2018

(54) PREPARATION METHOD OF POROUS CERAMIC, POROUS CERAMIC, AND ELECTRONIC CIGARETTE

(71) Applicants: Shenzhen Smoore Technology Limited, Shenzhen (CN); Hunan Zhengyuan Institute for Energy Storage Materials and Devices, Changsha (CN)

(72) Inventors: Pingkun Liu, Shenzhen (CN); Hongming Zhou, Changsha (CN); Jian Li, Changsha (CN); Qinglu Xia, Changsha (CN)

(73) Assignees: Shenzhen Smoore Technology Limited, Shenzhen (CN); Hunan Zhengyuan Institute for Energy Storage Materials and Devices, Changsha (CN)

( * ) Notice: Subject to any disclaimer, the term of this patent is extended or adjusted under 35 U.S.C. 154(b) by 500 days.

(21) Appl. No.: 14/414,114

(22) PCT Filed: Jun. 16, 2014

(86) PCT No.: PCT/CN2014/079963
§ 371 (c)(1),
(2) Date: Jan. 11, 2015

(87) PCT Pub. No.: WO2015/192300
PCT Pub. Date: Dec. 23, 2015

(65) Prior Publication Data
US 2015/0359262 A1     Dec. 17, 2015

(51) Int. Cl.
*C04B 35/14*     (2006.01)
*C04B 38/06*     (2006.01)
(Continued)

(52) U.S. Cl.
CPC .......... *A24F 47/008* (2013.01); *C04B 35/14* (2013.01); *C04B 35/6263* (2013.01);
(Continued)

(58) Field of Classification Search
CPC .......... C04B 35/14; C04B 2235/3217; C04B 2235/3272
See application file for complete search history.

(56) References Cited

U.S. PATENT DOCUMENTS

2002/0027316 A1* 3/2002 Ishikawa ............... B09B 3/0066
  264/669
2009/0250660 A1* 10/2009 Nayak .................. C04B 28/021
  252/182.32
(Continued)

FOREIGN PATENT DOCUMENTS

CN    1247174 A  *  3/2000
WO    WO-2016191798 A1 * 12/2016 ............. C03C 17/22

*Primary Examiner* — Erin Snelting
(74) *Attorney, Agent, or Firm* — Rosenberg, Klein & Lee

(57) ABSTRACT

The present invention relates to a preparation method of a porous ceramic, the porous ceramic, and a use thereof in the electronic cigarette. The method of preparing a porous ceramic includes: mixing amorphous silica, aluminum oxide and iron oxide uniformly to obtain a mixture; sintering the mixture at a temperature of 1000° C. to 1400° C. for 0.5 hour to 3 hours to obtain a precursor; grinding the precursor to obtain precursor powder; mixing the precursor powder, sodium silicate, and porogen uniformly to obtain a premix; mixing and extruding the premix with water to obtain a molded body; and heat preserving the molded body at a temperature of 200° C. to 600° C. for 1 hour to 6 hours, and sintering the molded body at a temperature of 700° C. to 1200° C. for 0.5 hour to 3 hours to obtain the porous ceramic.

7 Claims, 3 Drawing Sheets

(51) Int. Cl.
*A24F 47/00* (2006.01)
*C04B 38/00* (2006.01)
*C04B 35/626* (2006.01)

(52) U.S. Cl.
CPC .... *C04B 35/62685* (2013.01); *C04B 38/0054* (2013.01); *C04B 38/06* (2013.01); *C04B 2235/3201* (2013.01); *C04B 2235/3217* (2013.01); *C04B 2235/3272* (2013.01); *C04B 2235/3418* (2013.01); *C04B 2235/3427* (2013.01); *C04B 2235/5212* (2013.01); *C04B 2235/6562* (2013.01); *C04B 2235/96* (2013.01)

(56) References Cited

U.S. PATENT DOCUMENTS

| | | | |
|---|---|---|---|
| 2014/0283860 A1* | 9/2014 | Stolz | A24B 15/165 131/330 |
| 2014/0326260 A1* | 11/2014 | Gladden | A24B 15/165 131/329 |
| 2015/0040924 A1* | 2/2015 | Mironov | A24F 47/006 131/328 |
| 2016/0135495 A1* | 5/2016 | Poget | A24D 1/002 131/336 |

* cited by examiner

… (1) …

PREPARATION METHOD OF POROUS CERAMIC, POROUS CERAMIC, AND ELECTRONIC CIGARETTE

RELATED APPLICATIONS

This application is a §371 National Phase Application of International Application No. PCT/CN2014/079963, filed on Jun. 16, 2014.

FIELD OF THE INVENTION

The present disclosure relates to a preparation method of a porous ceramic, the porous ceramic, and a use thereof in the electronic cigarette.

BACKGROUND OF THE INVENTION

The porous ceramics are generally referred to as ceramic materials formed by sintering compositions consisting of aggregate, binder, and a porogen or other at a high temperature. Due to the features of high porosity, high chemical stability, high surface area, low bulk density, low thermal conductivity, high temperature resistance, corrosion resistance, and excellent performance, the porous ceramics are widely used in metallurgy, biotechnology, energy, environmental protection, and other fields.

The atomizer of an electronic cigarette is a main component for storing liquid and generating smoke, and there is a need to ensure that the liquid does not leak and a certain amount of smoke is generated. However, the porous ceramic prepared according to the conventional method cannot take into account both the strength and the porosity, and thus it cannot be applied to electronic cigarettes.

SUMMARY OF THE INVENTION

Accordingly, it is necessary to provide a preparation method of a porous ceramic with higher porosity and strength, the porous ceramic, and a use thereof in the electronic cigarette.

A method of preparing a porous ceramic includes the steps of:

mixing amorphous silica, aluminum oxide, and iron oxide uniformly to obtain a mixture, wherein the amount of the amorphous silica in the mixture is from 80% to 90% by mass, the amount of the aluminum oxide in the mixture is from 1% to 10% by mass, the amount of iron oxide in the mixture is from 1% to 10% by mass;

sintering the mixture at a temperature of 1000° C. to 1400° C. for 0.5 hour to 3 hours to obtain a precursor;

grinding the precursor to obtain a precursor powder;

mixing the precursor powder, sodium silicate, and porogen uniformly to obtain a premix, wherein the amount of the precursor powder in the premix is from 60% to 90% by mass, the amount of sodium silicate in the premix is from 0% to 20% by mass, the amount of porogen in the premix is from 10% to 40% by mass;

mixing and extruding the premix with water to obtain a molded body;

heat preserving the molded body at a temperature of 200° C. to 600° C. for 1 hour to 6 hours; and sintering the molded body at a temperature of 700° C. to 1200° C. for 0.5 hour to 3 hours to obtain the porous ceramic.

In one embodiment, after the precursor is ground, the precursor is passed through a 50-mesh standard sieve to obtain the precursor powder.

In one embodiment, the porogen is at least one selected from the group consisting of sucrose, starch, wood fiber, and short carbon fiber.

In one embodiment, a particle size of the sucrose and starch ranges from 10 μm to 150 μm; a diameter of the wood fiber and short carbon fiber ranges from 50 μm to 300 μm; a length of the wood fiber and short carbon fiber ranges from 300 μm to 3000 μm.

In one embodiment, a mass ratio of the premix and the water is 3:1 to 6:1.

In one embodiment, the extruding is performed under a pressure of 0.5 MPa to 20 MPa.

In one embodiment, heat preserving the molded body at the temperature of 200° C. to 600° C.[H] further comprises heating the molded body to the temperature of 200° C. to 600° C. with a heating rate of 1° C./min to 10° C./min.

A porous ceramic prepared by any one of the methods described above is provided.

In one embodiment, a porosity of the porous ceramic ranges from 40% to 80%, and a pore size of the porous ceramic ranges from 10 μm to 300 μm.

A use of a porous ceramic prepared by any one of the methods described above in an electronic cigarette.

The forgoing preparing method of the porous ceramics uses amorphous silica, aluminum oxide, and iron oxide as the aggregate of the porous ceramic, and the aggregate can be sintered at a low temperature, in an air atmosphere at atmospheric pressure, which is a relatively mild sintering condition. The aggregate is mixed before sintering, such that the resulting precursor has a loose structure, which will not produce pores blocking the liquid phase in the subsequent sintering process. The pores are difficult to be crushed during molding, thus ensuring the porosity of the porous ceramic. The pre-sintered precursor has a stable structure, which is favorable to improve the strength of porous ceramics, such that the prepared porous ceramic has a high porosity and good strength.

DETAILED DESCRIPTION OF THE EMBODIMENTS

Embodiments of the invention are described more fully hereinafter with reference to the accompanying drawings. The various embodiments of the invention may, however, be embodied in many different forms and should not be construed as limited to the embodiments set forth herein. Rather, these embodiments are provided so that this disclosure will be thorough and complete, and will fully convey the scope of the invention to those skilled in the art.

Figure 1:
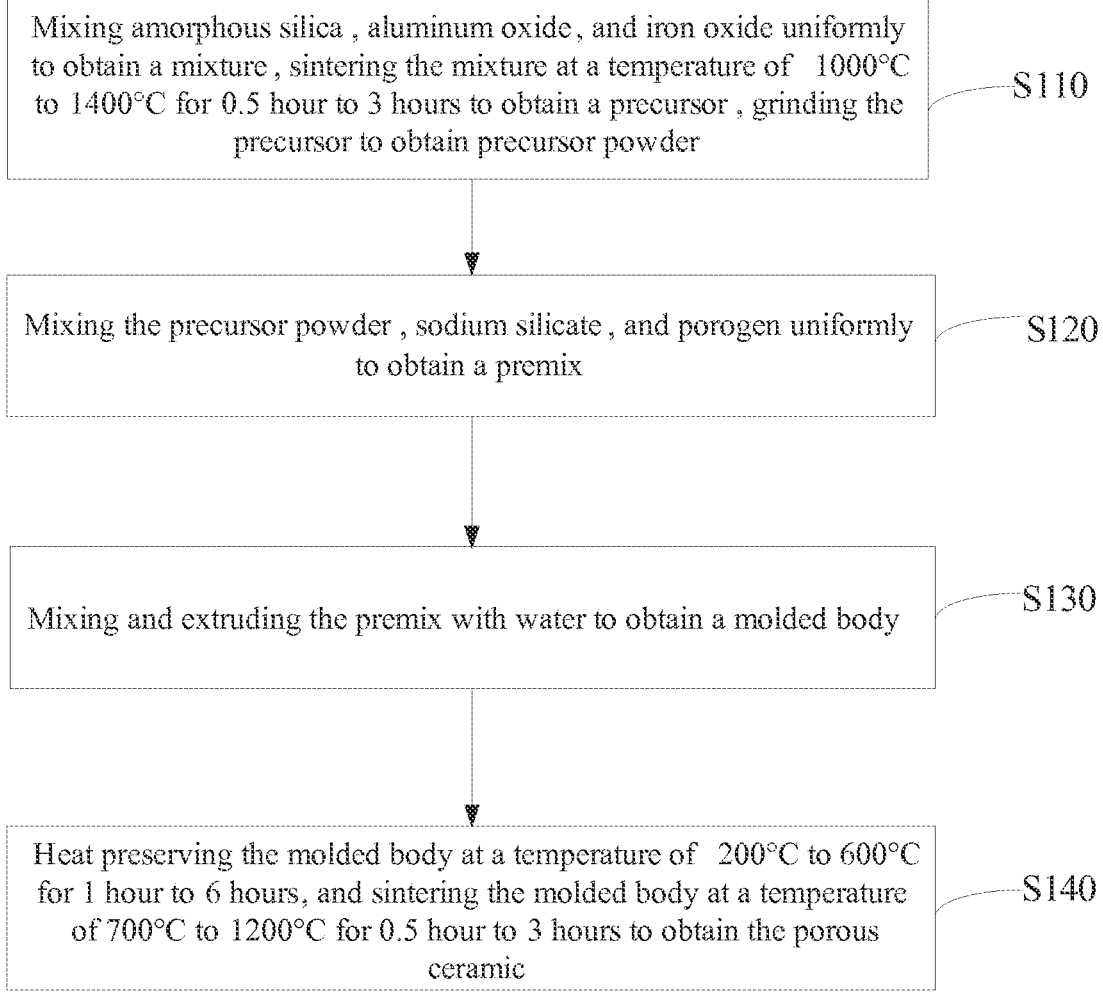
FIG. 1 is a flow chart of a method of preparing a porous ceramic according to one embodiment.

Referring to FIG. 1, a method of preparing a porous ceramic includes the steps of:

In step S110, amorphous silica, aluminum oxide and iron oxide are mixed uniformly to obtain a mixture, the mixture is then sintered at a temperature of 1000° C. to 1400° C. for 0.5 hour to 3 hours to obtain a precursor, and the precursor is ground to obtain precursor powder.

The amount of the amorphous silica ($SiO_2$) in the mixture is from 80% to 90% by mass. The amount of the aluminum oxide ($Al_2O_3$) in the mixture is from 1% to 10% by mass. The amount of iron oxide ($Fe_2O_3$) in the mixture is from 1% to 10% by mass.

Preferably, the amorphous silica, the aluminum oxide, and the iron oxide are of analytical grade.

Preferably, after the precursor is ground, the precursor is passed through a 50-mesh standard sieve to obtain the precursor powder. It is to be understood that other methods can be employed to obtain the precursor powder as long as the particle size of the precursor powder meets the requirements described.

Preferably, the sintering is performed in an oxidation furnace with high temperature and normal pressure.

Preferably, the amorphous silica, the aluminum oxide, and the iron oxide are dry mixed for 0.5 hour to 8 hours by a roller ball mill or a planetary ball mill. It is to be understood that, other methods can be employed to mix them as long as they are uniformly mixed, for example, they can be dry mixed by a blender or a kneader for 2 minutes to 2 hours.

In this step, the precursor obtained by pre-sintering the mixture has a loose structure.

Step 120, the precursor powder, sodium silicate, and porogen are uniformly mixed to obtain a premix.

The amount of the precursor powder in the premix is from 60% to 90% by mass. The amount of sodium silicate in the premix is from 0% to 20% by mass. The amount of porogen in the premix is from 10% to 40% by mass.

In the illustrated embodiment, the sodium silicate ($Na_2SiO_3$) mixed with the precursor powder and the porogen can take a form of $Na_2SiO_3$, $Na_2SiO_3 \cdot 9H_2O$; or aqueous solution of sodium silicate with a modulus of 1.5 to 3.5, as long as the mass ratio between the sodium silicate in the $Na_2SiO_3 \cdot 9H_2O$ or aqueous solution of sodium silicate and the other raw material (precursor powder and porogen) remains the same.

In the illustrated embodiment, the porogen is at least one material selected from the group consisting of sucrose, starch, wood fiber, and short carbon fiber. Preferably, a particle size of the sucrose and starch ranges from 10 µm to 150 µm; a diameter of the wood fiber and short carbon fiber ranges from 50 µm to 300 µm; a length of the wood fiber and short carbon fiber ranges from 300 µm to 3000 µm.

Preferably, the precursor powder, sodium silicate, and porogen are dry mixed for 0.5 hour to 8 hours by a roller ball mill or a planetary ball mill. It is to be understood that, in an alternative embodiment, they can be dry mixed by a blender or a kneader for 10 minutes to 2 hours.

In step S120, since complex organic or inorganic substances with large particle diameters, such as sucrose, starch, wood fiber, and short carbon fiber are used as porogen, the pore size and porosity of the finally obtained porous ceramic can be controlled according to the demand, thus obtaining a communicating channel structure adopted for storing, liquid conducting, and smoke generating.

In step S130, the premix and water are mixed and extruded to obtain a molded body.

Preferably, a mass ratio of the premix and the water is 3:1 to 6:1.

Preferably, the extruding is performed under a pressure of 0.5 MPa to 20 MPa.

In the illustrated embodiment, the premix and the water are mixed to form a semi-moist material, which is then placed into a cylindrical mold and extruded under a pressure of 0.5 MPa to 20 MPa to form a cylindrical molded body. It is to be understood that the shape of the molded body is not limited to be cylindrical but depends on the shape of the final product.

In step S130, as the premix is mixed with the water, certain porogens in the premix exhibit a viscosity subjected to water, and the sodium silicate solution also has a certain viscosity and serves as a forming agent, thus simplifying the composition of raw materials and production processes, and reduces costs.

In step S140, the molded body is heat preserved at a temperature of 200° C. to 600° C. for 1 hour to 6 hours, and then sintered at a temperature of 700° C. to 1200° C. for 0.5 hour to 3 hours to obtain the porous ceramic.

Preferably, the molded body is heated to a temperature of 200° C. to 600° C. with a heating rate of 1° C./min to 10° C./min, then the molded body is heat preserved at a temperature of 200° C. to 600° C. for 1 hour to 6 hours.

In the illustrated embodiment, the sintering at 700° C. to 1200° C. is carried out at atmospheric pressure.

Preferably, the heat preserving and sintering are performed in an oxidation furnace with a high temperature and normal pressure.

A porosity of the final obtained porous ceramic ranges from 40% to 80%; and a pore size of the porous ceramic ranges from 10 µm to 300 µm.

The forgoing preparing method of the porous ceramics uses amorphous silica, aluminum oxide, and iron oxide as the aggregate of the porous ceramic, and the aggregate can be sintered at a low temperature, in an air atmosphere at atmospheric pressure, which is a relatively mild sintering condition. The aggregate is mixed before sintering, such that the resulting precursor has a loose structure, which will not produce pores blocking the liquid phase in the subsequent sintering process. The pores are difficult to be crushed during molding, thus ensuring the porosity of the porous ceramic. The pre-sintered precursor has a stable structure, which is favorable to improve the strength of porous ceramics. The prepared porous ceramic has a good strength and a high porosity. Thus, when the prepared porous ceramic is applied to an atomizer of an electronic cigarette, the structure of the atomizer can be simplified. Since the porous ceramics can store more liquid and exhibit a better liquid atomization, cost is reduced. In addition, the preparation method for the porous ceramics is simple, requires low sintering temperature, and is safe and nontoxic.

Figure 2:
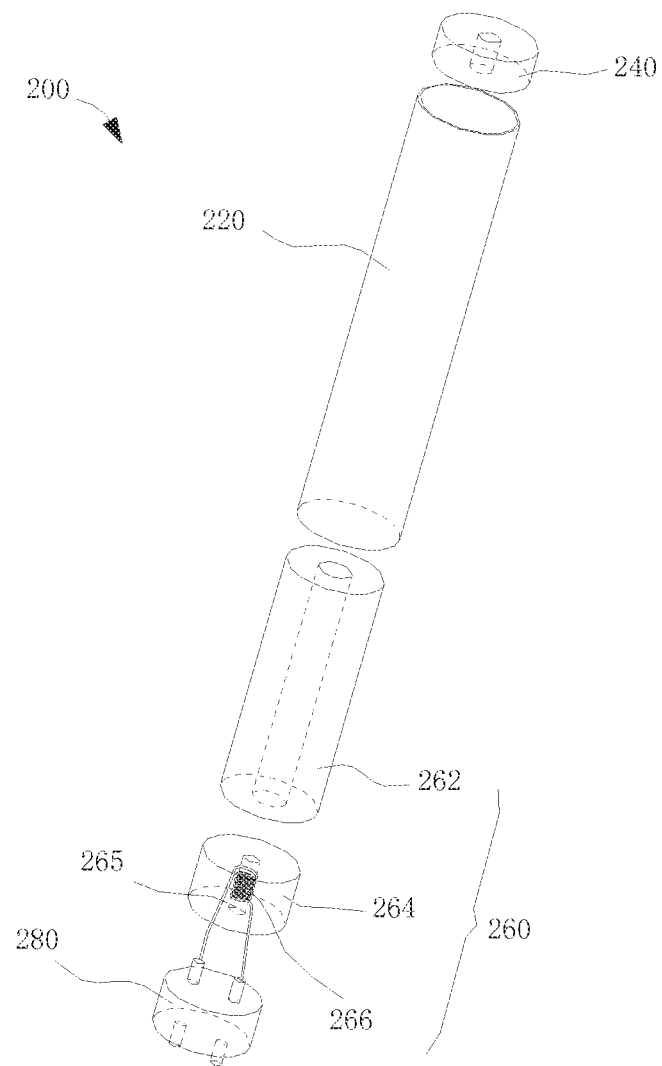
FIG. 2 is a perspective view of an electronic cigarette according to one embodiment.
Figure 3:
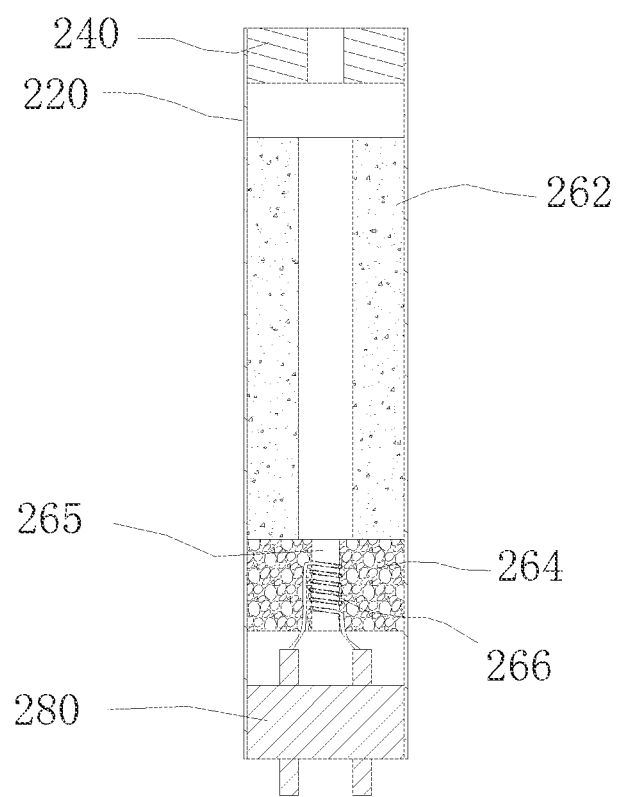
FIG. 3 is a cross-sectional view of the electronic cigarette of FIG. 2.

Referring to FIG. 2 and FIG. 3, an embodiment of an electronic cigarette 200 includes a housing 220, a mouthpiece cover 240, an atomizing assembly 260, and a power assembly 280. The atomizing assembly 260 includes a liquid reservoir 262 and a liquid absorbing element 264. The liquid absorbing element 264 is shaped as a cylinder matching with the housing 220. The liquid absorbing element 264 can be made of the porous ceramic prepared according to the forgoing method. The liquid absorbing element 264 is received in the housing 220 and positioned at an end of the liquid reservoir 262. The liquid from the liquid reservoir 262 can be uniformly dispersed to the inside and the surface of the liquid absorbing element 264 by capillary action. The liquid absorbing element 264 defines an atomizing channel 265 therein communicated with the smoke channel of the electronic cigarette 200. The heating element 266 is a helical heating wire received in the atomizing channel 265.

It should be noted that when the porous ceramic, prepared according to the forgoing method, is used as the liquid absorbing element of the electronic cigarette, the structures of the electronic cigarette and liquid absorbing element may not be limited to that of the above description. Other types of electronic cigarettes can use the porous ceramic as a liquid absorbing element as long as the shape of the liquid absorbing element is adjusted according to the shape of the electronic cigarette. The prepared porous ceramic has a high pore size, high porosity, and a good strength, thus it can store more liquid and exhibit a better liquid atomization, which on the one hand can reduce the cost, and on the other hand can exhibit a long life use with better performance.

Reference will now be made to describe, in detail, embodiments of the present preparation method of porous ceramic.

The performance test method for the porous ceramic according to the present embodiment are: using Archimedes drainage method to test the porosity of the porous ceramic; using an electronic universal testing machine to test the bending strength of the sample (GB/T 4741-1999); using a pore size distribution measuring instrument to test the average pore diameter of the porous ceramic.

Example 1

80 g of $SiO_2$, 10 g of $Al_2O_3$, and 10 g of $Fe_2O_3$ were weighed and ground by a planetary ball mill for 2 hours. The mixture was sintered in a high temperature furnace at a temperature of 1200° C. for 1 hour. The sintered mixture was ground and passed through a 50-mesh standard sieve to obtain the precursor powder. 90 g of precursor powder and 10 g of wood fiber (porogen) were weighed and mixed with stirring for 30 minutes to obtain a mixed premix, in which a diameter of the wood fiber was 300 μm, and a length of the wood fiber was 1 mm to 3 mm. The premix and the water were mixed according to a mass ratio of 3:1 and stirred for 5 minutes to obtain a semi-moist material, then the semi-moist material was placed into a cylindrical mold and extruded under a pressure of 0.5 MPa to form a desired molded body. The molded body was placed into a resistance furnace, heated to 600° C. with a heating rate of 2° C./min, and heat preserved for 1 hour to remove the porogen and water. The sample was then sintered to 1000° C. for 1 hour with a heating rate of 2° C./min, and the furnace was cooled to obtain the desired porous ceramic. Tests on the porous ceramic article showed that the porosity was 36.1%, the bending strength was 15.60 MPa, and the average pore diameter was 200 μm.

Example 2

98 g of $SiO_2$, 1 g of $Al_2O_3$, and 1 g of $Fe_2O_3$ were weighed and ground by a planetary ball mill for 1 hour. The mixture was sintered in a high temperature furnace at a temperature of 1000° C. for 3 hours. The sintered mixture was ground and passed through a 50-mesh standard sieve to obtain the precursor powder. 60 g of precursor powder and 40 g of starch (porogen) were weighed and ground by a planetary ball mill for 0.5 hour to obtain a mixed premix, in which a particle size of the starch was 20 μm. The premix and the water were mixed according to a mass ratio of 6:1 and stirred for 5 minutes to obtain a semi-moist material, then the semi-moist material was placed into a cylindrical mold and extruded under a pressure of 20 MPa to form a desired molded body. The molded body was placed into a resistance furnace, firstly heated to 200° C. with a heating rate of 1° C./min and heat preserved for 2 hours, then heated to 600° C. with the same heating rate and heat preserved for 4 hours to remove the porogen and water. The sample was then sintered to 700° C. for 3 hours with a heating rate of 1° C./min, and the furnace was cooled to obtain the desired porous ceramic. Tests on the porous ceramic article showed that the porosity was 65.3%, the bending strength was 10.53 MPa, and the average pore diameter was 20 μm.

Example 3

90 g of $SiO_2$, 5 g of $Al_2O_3$, and 5 g of $Fe_2O_3$ were weighed and ground by a planetary ball mill for 3 hours. The mixture was sintered in a high temperature furnace at a temperature of 1400° C. for 0.5 hour. The sintered mixture was ground and passed through a 50-mesh standard sieve to obtain the precursor powder. 70 g of precursor powder, 20 g of sodium silicate, and 10 g of short fiber (porogen) were weighed and ground by a planetary ball mill for 8 hours to obtain a mixed premix, in which a diameter of the short fiber was 50 μm, and a length of the short fiber was 300 μm. The premix and the water were mixed according to a mass ratio of 3:1 and stirred for 5 minutes to obtain a semi-moist material, then the semi-moist material was placed into a cylindrical mold and extruded under a pressure of 10 MPa to form a desired molded body. The molded body was placed into a resistance furnace, firstly heated to 300° C. with a heating rate of 10° C./min and heat preserved for 4 hours, then heated to 500° C. with the same heating rate and heat preserved for 2 hours to remove the porogen and water. The sample was then sintered to 1200° C. for 0.5 hour with a heating rate of 10° C./min, and the furnace was cooled to obtain the desired porous ceramic. Tests on the porous ceramic article showed that the porosity was 54.3%, the bending strength was 15.27 MPa, and the average pore diameter was 50 μm.

According to Examples 1 to 3, it can be inferred that the porous ceramic prepared according to the present method has a high porosity and a good physical strength.

Although the present invention has been described with reference to the embodiments thereof and the best modes for carrying out the present invention, it is apparent to those skilled in the art that a variety of modifications and changes may be made without departing from the scope of the present invention, which is intended to be defined by the appended claims.

What is claimed is:

1. A method of preparing a porous ceramic, comprising the steps of:
    mixing amorphous silica, aluminum oxide, and iron oxide uniformly to obtain a mixture, wherein the amount of the amorphous silica in the mixture is from 80% to 90% by mass, the amount of the aluminum oxide in the mixture is from 1% to 10% by mass, the amount of iron oxide in the mixture is from 1% to 10% by mass;
    sintering the mixture at a temperature of 1000° C. to 1400° C. for 0.5 hour to 3 hours to obtain a precursor;
    grinding the precursor to obtain a precursor powder;
    mixing the precursor powder, sodium silicate, and porogen uniformly to obtain a premix, wherein the amount of the precursor powder in the premix is from 60% to 90% by mass, the amount of sodium silicate in the premix is from 0% to 20% by mass, the amount of porogen in the premix is from 10% to 40% by mass;
    mixing and extruding the premix with water to obtain a molded body;
    heat preserving the molded body at a temperature of 200° C. to 600° C. for 1 hour to 6 hours; and
    sintering the molded body at a temperature of 700° C. to 1200° C. for 0.5 hour to 3 hours to obtain the porous ceramic.

2. The method according to claim 1, wherein after the precursor is ground, the precursor is passed through a 50-mesh standard sieve to obtain the precursor powder.

3. The method according to claim 1, wherein the porogen is at least one selected from the group consisting of sucrose, starch, wood fiber, and short carbon fiber.

4. The method according to claim 3, wherein a particle size of the sucrose and starch ranges from 10 μm to 150 μm; a diameter of the wood fiber and short carbon fiber ranges from 50 μm to 300 μm; a length of the wood fiber and short carbon fiber ranges from 300 μm to 3000 μm.

5. The method according to claim 1, wherein a mass ratio of the premix and the water is 3:1 to 6:1.

6. The method according to claim 1, wherein the extruding is performed under a pressure of 0.5 MPa to 20 MPa.

7. The method according to claim 6, wherein heat preserving the molded body at the temperature of 200° C. to 600° C. further comprises heating the molded body to the temperature of 200° C. to 600° C. with a heating rate of 1° C./min to 10° C./min.

\* \* \* \* \*